US008883452B2

(12) United States Patent
Wang et al.

(10) Patent No.: US 8,883,452 B2
(45) Date of Patent: Nov. 11, 2014

(54) K5 HEPAROSAN FERMENTATION AND PURIFICATION

(75) Inventors: Zhenyu Wang, Hamilton, OH (US); Robert J. Linhardt, Albany, NY (US); Jonathan S. Dordick, Schenectady, NY (US); Ujjwal Bhaskar, Troy, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 19 days.

(21) Appl. No.: 13/261,193

(22) PCT Filed: Aug. 30, 2010

(86) PCT No.: PCT/US2010/047183
§ 371 (c)(1),
(2), (4) Date: Feb. 28, 2012

(87) PCT Pub. No.: WO2011/028668
PCT Pub. Date: Mar. 10, 2011

(65) Prior Publication Data
US 2012/0157669 A1    Jun. 21, 2012

Related U.S. Application Data

(60) Provisional application No. 61/275,675, filed on Sep. 1, 2009.

(51) Int. Cl.
*C08B 37/10* (2006.01)
*C12P 19/28* (2006.01)
*C08B 37/00* (2006.01)
*C12P 19/26* (2006.01)

(52) U.S. Cl.
CPC ............ *C08B 37/0063* (2013.01); *C12P 19/26* (2013.01); *C08B 37/0003* (2013.01)
USPC ................. 435/85; 435/41; 435/84; 435/243; 435/252.1; 435/252.33

(58) Field of Classification Search
None
See application file for complete search history.

(56) References Cited

U.S. PATENT DOCUMENTS

| 5,550,116 A * | 8/1996 | Lormeau et al. ................. 514/56 |
| 2005/0233453 A1 | 10/2005 | Kariya et al. |
| 2007/0117188 A1 | 5/2007 | DeAngelis et al. |

FOREIGN PATENT DOCUMENTS

| JP | 2004-018840 A | 1/2004 |
| WO | WO 2005/014656 A1 | 2/2005 |
| WO | WO 2009/014559 A2 | 1/2009 |

OTHER PUBLICATIONS

Korz, DJ; et al; "Simple fed-batch technique for high cell density cultivation of *Escherichia coli*" Journal of Biotechnology, 39, 59-65, 1995.*

Kweon, Dong-Keon; et al; "Preparation of water-soluble chitosan/heparin complex and its application as wound healing accelerator" Biomaterials, 24, 1595-1601, 2003.*

Muzzarelli, RAA; Muzzarelli, C; "Chitosan Chemistry: Relevance to the Biomedical Sciences" Advanced Polymer Science, 186, 151-209, 2005.*

Williams, Kevin L; Endotoxins: Pyrogens, LAL Testing and Depyrogenation, Chapter 15, Informa Healthcare, New York, 2007.*

Bitter et al., "A Modified Uronic Acid Carbazole Reaction." Analytical Biochemistry, 1962, 4(4):330.

Finke A et al., "Biosynthesis of the *Escherichia coli* K5 polysaccharide, a representative of group II capsular polysaccharides: polymerization in vitro and characterization of the product" J Bacteriol, 1991, 173(13):4088-94.

Guerrini, et al., "Oversulfated chondroitin sulfate is a contaminant in heparin associated with adverse clinical events." Nature Biotechnology, 2008, 26, 669-675.

Han et al., "Structural snapshots of heparin depolymerization by heparin lyase I" J Biol Chem, 2009, 284(49):34019-27.

Hodson N et al., "Identification that KfiA, a protein essential for the biosynthesis of the *Escherichia coli* K5 capsular polysaccharide, is an alpha -UDP-GlcNAc glycosyltransferase. The formation of a membrane-associated K5 biosynthetic complex requires KfiA, KfiB, and KfiC." J Biol Chem, 2000, 275(35):27311-5.

Jann B, Jann K., "Structure and biosynthesis of the capsular antigens of *Escherichia coli*" Curr Top Microbiol Immunol, 1990, 150:19-42.

Legoux et al., "N-Acetyl-Heparosan Lyase of Scherichia coli K5: Gene Cloning and Expression," Journal of Bacteriology, 1996, 178(24):7260-7264.

Lindahl et al., "Generation of "Neoheparin" from *E coli* K5 capsular polysaccharide" J Med Chem, 2005, 48(2):349-352.

Lindahl et al., "Regulated diversity of heparan sulfate," J Biol Chem, 1998, 273(39):24979-24982.

Linhardt et al., "Role of glycosaminoglycans in cellular communication," Acc Chem Res, 2004, 37: 431-438.

Linhardt, Robert J., "Heparin: an important drug enters its seventh decade." Chem. Ind. 2, 45-50 (1991).

Linhardt, Robert J., "Heparin: structure and activity," J Med Chem, 2003, 46: 2551-2554.

Ly et al., "Analysis of *E. coli* K5 capsular polysaccharide heparosan," Anal. Bioanal. Chem., published online Apr. 21, 2010, 399:737-745.

Manzoni M et al., "Extracellular K5 Polysaccharide of *Escherichia coli*: Production and Characterization," Journal of Bioactive and Compatible Polymers, Jul. 1993, 8(3):251-257.

Manzoni M et al., "Production of K5 polysaccharides of different molecular weight by *Escherichia coli*" Journal of Bioactive and Compatible Polymers, 1996, 11(4):301-311.

Manzoni M, et al., "Influence of the culture conditions on extracellular lyase activity related to K5 polysaccharide." Biotechnology Letters, 2000, 22(1):81-85.

(Continued)

*Primary Examiner* — Blaine Lankford
*Assistant Examiner* — David Berke-Schlessel
(74) *Attorney, Agent, or Firm* — Foley & Lardner LLP

(57) ABSTRACT

A method for the production of heparosan from fermentation culture of *E. coli* K5 suitable for industrial production, exhibiting superior yield and purity, smaller culture volumes, faster growth, and lower costs.

16 Claims, 11 Drawing Sheets

(56) References Cited

OTHER PUBLICATIONS

McNulty C et al., "The cell surface expression of group 2 capsular polysaccharides in *Escherichia coli*: the role of KpsD, RhsA and a multi-protein complex at the pole of the cell" Mol Microbiol, 2006, 59(3):907-22.

Song J-M et al., "A simple method for hyaluronic acid quantification in culture broth" Carbohydrate Polymers, 2009, 78:633-634.

Vann WF et al., "The structure of the capsular Polysaccharide (K5 Antigen) of Urinary-Tract-Infective *Escherichia-Coli* 010-K5-H4—a Polymer Similar to Desulfo-Heparin" European Journal of Biochemistry, 1981, 116(2):359-364.

Wang et al., "*E. coli* K5 Fermentation and the Preparation of Heparosan, a Bioengineered Heparin Precursor," Biotechnology and Bioengineering, published online Aug. 17, 2010, 107(6):964-973.

Wang et al., "High cell density culture of metabolically engineered *Escherichia coli* for the production of poly(3-hydroxybutyrate) in a defined medium" Biotechnology and Bioengineering, 1998, 58(2-3):325-328.

Wang et al., "Nuclear magnetic resonance quantification for monitoring heparosan K5 capsular polysaccharide production," Anal Biochem., 2009, 398(2):275-277.

Zhang et al., "Solution structures of chemoenzymatically synthesized heparin and its precursors" Journal of the American Chemical Society, 2008, 130(39):12998-13007.

\* cited by examiner

K5 HEPAROSAN FERMENTATION AND PURIFICATION

CROSS REFERENCE TO RELATED APPLICATIONS

This application is a National Stage application of PCT/US2010/047183, filed Aug. 30, 2010, which claims priority to U.S. Provisional Patent Application No. 61/275,675, filed Sep. 1, 2009, which is entirely incorporated by reference herein.

GOVERNMENT LICENSE RIGHTS

This invention was made with U.S. Federal Government support under grants GM38060 and HL096972 awarded by National Institutes of Health. The U.S. Federal Government has certain rights in the invention.

BACKGROUND

Heparin and heparan sulfate are biologically important molecules involved in blood anticoagulation, viral and bacterial infection, angiogenesis, inflammation, cancer and development. Linhardt (2003) "Heparin: structure and activity," *J Med Chem,* 46: 2551-2554. Linhardt R J, Toida T. (2004) "Role of glycosaminoglycans in cellular communication," *Acc Chem Res,* 37: 431-438. Heparin finds a wide spectrum of applications including surgery, heart-lung oxygenation and kidney dialysis, treatment of deep vein thrombosis and acute coronary syndrome. Linhardt "Heparin: an important drug enters its seventh decade." *Chem. Ind.* 2, 45-50 (1991); Agnelli et al. "Enoxaparin plus compression stockings compared with compression stockings alone in the prevention of venous thromboembolism after elective neurosurgery" *N Engl J Med* 339 (2), 80-5 (1998). Heparin is also coated on the surface of blood vessels and medical devices such as test tubes and rental dialysis machines, to form an anticoagulant surface.

Heparin is currently prepared from animal tissues in amounts of approximately 100 metric tons/year, but such heparin may be contaminated with other biological products. Linhardt *Chem. Ind.* 2, 45-50 (1991). Heparin contaminated with oversulfated chondroitin sulfate led to the death of nearly 100 Americans in 2008. Guerrini, et al. "Oversulfated chondroitin sulfate is a contaminant in heparin associated with adverse clinical events." *Nature Biotechnology* 26, 669-675 (2008).

The natural eukaryotic heparin biosynthesis precursor, heparosan, is a polysaccharide with the repeating diassachride unit [→4) β-D-glucuronic acid (GlcA) (1→4) N-acetyl-α-D-glucosamine (GlcNAc) (1→]$_n$, shown in FIG. 1.

Heparosan is also biosynthesized as a polysaccharide capsule in bacteria including *Escherichia coli* K5 and *Pasteurella multicida.* Lindahl U et al. (1998) "Regulated diversity of heparan sulfate" *J Biol Chem* 273(39):24979-24982. The initiation of K5 heparosan synthesis reportedly involves 2-keto-3-deoxyoctulosonic acid. Finke A et al. (1991) "Biosynthesis of the *Escherichia coli* K5 polysaccharide, a representative of group II capsular polysaccharides: polymerization in vitro and characterization of the product" *J Bacteriol* 173(13): 4088-94. K5 heparosan is then elongated through the alternate action of the glycotransferases KfiA and KfiC that add GlcNAc and GlcA to the nonreducing end of the growing polysaccharide chain. Hodson N et al. (2000) "Identification that KfiA, a protein essential for the biosynthesis of the *Escherichia coli* K5 capsular polysaccharide, is an alpha-UDP-GlcNAc glycosyltransferase. The formation of a membrane-associated K5 biosynthetic complex requires KfiA, KfiB, and KfiC." *J Biol Chem* 275(35):27311-5. Once synthesized, the heparosan chain is transported onto the cell surface through a pathway consisting of six proteins: KpsC, KpsD, KpsE, KpsM, KpsS and KpsT. McNulty C et al (2006) "The cell surface expression of group 2 capsular polysaccharides in *Escherichia coli:* the role of KpsD, RhsA and a multi-protein complex at the pole of the cell" *Mol Microbiol* 59(3):907-22. The K5 heparosan chain is believed to be anchored on the cell surface through lipid substitution at the reducing end of the polysaccharide to a phosphatidic acid molecule in the outer membrane of *E. coli.* Jann B, Jann K. (1990) "Structure and biosynthesis of the capsular antigens of *Escherichia coli"* *Curr Top Microbiol Immunol* 150:19-42. Portions of the heparosan polysaccharide can be shed from *E. coli* K5 through the action of K5 heparosan lyase, an enzyme originating from a bacterial phage that cleaves the heparosan chain through a β-elimination mechanism. Manzoni M et al. (1996) "Production of K5 polysaccharides of different molecular weight by *Escherichia coli"* *Journal of Bioactive and Compatible Polymers* 11(4):301-311. Manzoni M, et al. (2000) "Influence of the culture conditions on extracellular lyase activity related to K5 polysaccharide." *Biotechnology Letters* 22(1):81-85. The gene encoding K5 lyase is integrated into the *E. coli* K5 DNA and its expression may be inducible. Manzoni M, et al. (2000). *Biotechnology Letters* 22(1):81-85. The activity of K5 lyase can affect the amount of heparosan released into the culture medium as well as the structure and molecular weight properties of both the cell associated and released heparosan (FIG. 1B). K5 heparosan has been estimated to have a $M_w$ 20,000 and comprised of two major subcomponents with $M_w$ 16,000 and 1,500. The ratio of the two subcomponents corresponds to the overall $M_w$ and is influenced by the activity of the K5 lyase Vann W F et al (1981) "The structure of the capsular Polysaccharide (K5 Antigen) of Urinary-Tract-Infective *Escherichia-Coli* 010-K5-H4—a Polymer Similar to Desulfo-Heparin" *European Journal of Biochemistry* 116(2):359-364; Manzoni (2000) *Biotechnology Letters* 22(1):81-85.

Laboratory-scale studies have shown that heparosan with a weight average molecular weight ($M_w$)>10,000, obtained from *E. coli* K5 strain can be enzymatically converted to an anticoagulant polysaccharide similar to heparin. Lindahl et al. (2005) "Generation of "Neoheparin" from *E coli* K5 capsular polysaccharide" *J Med Chem* 48(2):349-352; Zhang et al. (2008) "Solution structures of chemoenzymatically synthesized heparin and its precursors" *Journal of the American Chemical Society* 130(39):12998-13007. Heparosan may also be used in a variety of applications (WO 2009/014559).

The present invention describes a process of *E. coli* K5 fermentation with a high yield of heparosan and efficient recovery of high purity heparosan suitable for industrial production of heparosan.

SUMMARY OF THE INVENTION

The present invention concerns improved methods for the production of heparosan by fermentation of *E. coli* K5, isolation of the K5 polysaccharide, and purification.

In one embodiment, the method comprises (a) culturing *E. coli* K5 in defined medium with glucose as the primary carbon source; (b) binding heparosan to a solid phase with subsequent elution; and (c) precipitating heparosan from the eluate. The method is suitable for the production of substantially pure heparosan, which is at least 90% pure.

In related embodiments, the method comprises two phases of culturing, namely a batch growth phase and fed batch growth stage, wherein (a) the medium used in the batch growth stage comprises (per liter) about 20 g glucose, 10-300 mg thiamine, about 13.5 g $KH_2PO_4$; about 4.0 g $(NH_4)_2HPO_4$, about 1.4 g $MgSO_4.7H_2O$, about 1.7 g citric acid, and about 10.0 mL trace metal solution (per liter); wherein the trace metal solution consists essentially of (per L of 5 M HCl) 10.0 g $FeSO_4.7H_2O$, 2.0 g $CaCl_2$, 2.2 g $ZnSO_4.7H_2O$, 0.5 g $MnSO_4.4H_2O$, 1.0 g $CuSO_4.5H_2O$, 0.1 g $(NH_4)_6Mo_7O_{24}.4H_2O$, and 0.02 g $Na_2B_4O_7.10H_2O$ and wherein; (b) the feeding solution used in the fed batch growth stage consists of (per L): 250-1000 g glucose, about 20 g $MgSO_4.7H_2O$ and 0.15-0.5 g thiamine, and optionally about 47 g $KH_2PO_4$.

In related embodiments, oxygen is provided by sparged air. The air may be supplemented with oxygen. Preferably, dissolved oxygen is maintained at about 20%. In some embodiments, pure oxygen is used.

In further related embodiments, the conditions include the temperature maintained at about 37° C., and the pH is maintained at about 7. The pH may be maintained by the addition of an ammonia solution, or ammonia gas. In some embodiments, the ammonia solution is about 25-35%, including about 30%, such as 29%.

In particular embodiments, the feeding medium used in the fed-batch stage is fed at a rate determined by $$Ms(t) = F(t)s_{F(t)} = \left(\frac{\mu}{Y_{\frac{x}{s}}} + m\right)X(t_0)V(t_0)\exp[\mu(t-t_0)]$$

wherein MS is mass flow rate of the carbon source (g/h); F is feed flow rate (L/h); $S_F$ is carbon substrate concentration in the feed (g/L); X is cell concentration (g/L dcw); m is specific maintenance coefficient (g/g dcw/h); V is culture volume (L); $t_0$ is time of feeding start; t is process time; $\mu$ is specific growth rate ($h^{-1}$); and $Y_{x/s}$ is cell yield on carbon substrate (g/g).

The method also encompasses binding and elution of heparosan from the culture medium. In one embodiment, heparosan is obtained from the cell-free supernatant. In another embodiment, heparosan is obtained from cells by washing with a detergent solution, such as SDS (e.g., 1% SDS), with agitation.

After removal of the cells, binding and elution may include mixing of an anionic exchange resin with the culture supernatant and removal of the supernatant, washing the resin with 50 mM sodium chloride in sodium acetate buffer at pH 4, elution with 1 M sodium chloride in sodium acetate buffer at pH 4.

Alternatively, binding and elution may be achieved with chitosan. In one embodiment, the culture supernatant is mixed with a chitosan solution which is allowed to precipitate. The precipitate is isolated, washed, such as with water or other dilute buffer, and eluted with strong base, such as about 1M NaOH. Binding and elution with chitosan may be performed in addition to anionic exchange.

Following binding and elution, the heparosan is precipitated from the eluate, such as with ethanol or methanol. In one embodiment, 3 volumes of ethanol are used. The resulting precipitate is typically washed, and dried.

The method also encompasses an optional depyrogenation step, such as by oxidation, including with hydrogen peroxide.

The method of the invention obtains high yields of heparosan, with high purity, in small culture volumes, in a short period of time, and with low amounts of contaminants. Thus, the invention is suitable for industrial production of heparosan. The yield of heparosan may be obtained in a fermentation of less than 60 hours, less than 48 hours, and less than 40 hours, not including the growth of starter culture. In other embodiments, the initial culture volume is 3 L at batch phase, working to 7 L in the fed phase, and similar ratios. In related embodiments, therefore, the culture produces at least 10 g/L, at least 11 g/L, at least 12 g/L, at least 13 g/L, at least 14 g/L, and at least 15 g/L of heparosan. The substantially pure heparosan is at least 90%, at least 95%, at least 97%, or at least 99% pure. In related embodiments, the heparosan is less than 1% DNA and less than 2% protein. The heparosan is suitable for processing into heparin. In one embodiment, the heparosan has a number average molecular weight of at least 10, 20, 30, 40, 50, or 60 kDa, such as about 58 kDa; a weight average molecular weight of at least 20, 30, 40, 50, 60, 70, 80 or 90 kDa, such as about 84 kDa, and polydispersity index (PDI) less than 2.0, including less than 1.9, 1.8, 1.7, 1.6, 1.5, 1.4, or 1.3, including about 1.4.

In further embodiments, the invention includes the use of the heparosan produced by the above methods in a pharmaceutical preparation, such as a coating of a medical device. In related embodiments, the heparosan is used for the production of heparin. Relatedly, the invention is a method of use of the heparosan or heparin produced by the foregoing method for the manufacture of a medicament.

In further embodiments, the invention is heparosan produced by the foregoing method, including heparosan with a purity of at least 90%, at least 95%, and more. In related embodiments, the invention is heparin produced from said heparosan.

DETAILED DESCRIPTION OF THE INVENTION

Definitions

Figure 1:
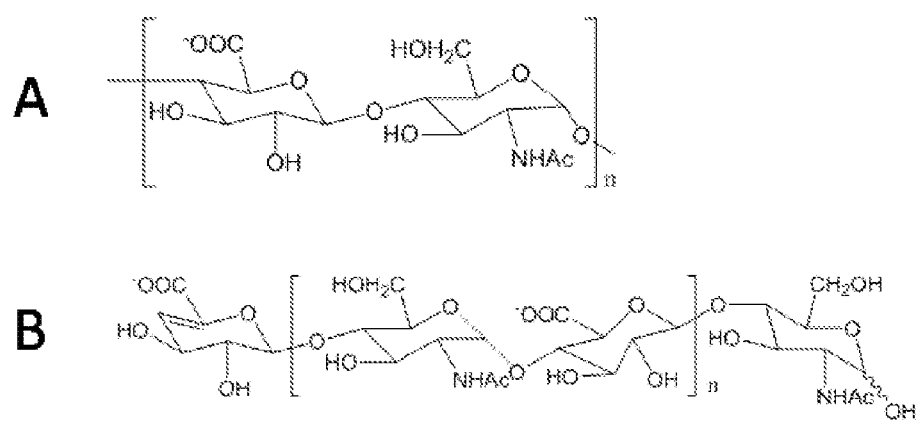
FIG. 1. Structure of heparosan. A. repeating disaccharide unit of heparosan B. structure of heparosan chain resulting from the action of heparosan K5 lyase.

Heparosan is a polysaccharide with the repeating diassachride unit [GlcAα-(1-4)GlcNAcR(1-4)]$_n$. Because the K5 exopolysaccharide is made from heparosan, which the present inventors isolate and purify, "heparosan" in certain contexts can refer to heparosan associated with bacteria, present in culture medium, and during isolation and purification. The meaning of heparosan will be understood by the person of ordinary skill in the relevant context.

*Escherichia coli* K5 describes variants of *E. coli* that produce the K5 exopolysaccharide. Suitable *E. coli* K5 strains may be obtained from public collections such as ATCC (American Type Culture Collection, USA), such as *E. coli* strain ATCC23506. *Escherichia coli* K5 strains may be also be isolated from clinical sources, and/or genetically modified.

As used herein "fermentation" refers to bacterial growth and production of exopolysaccharide, in particular the K5 exopolysaccharide.

As used herein "isolated" means the heparosan is separated from the culture medium and bacterial cells and present in sufficient quantity to permit its identification or use.

As used herein "substantially pure" means that the heparosan is essentially free of other substances to an extent practical and appropriate for its intended use. A substantially pure heparosan is at least 90% pure. Preferably, the material is greater than 91%, 92%, 93%, 94%, 95%, 96%, 97%, 98%, or even greater than 99% free of contaminants. The degree of purity may be assessed by means known in the art.

As used herein "a" or "an" means one or more, unless specifically indicated to mean only one.

The term "about" is used as understood by the person of skill in the art in the context to which the "about" modifies the stated term. For a numerical value, "about" may be considered to encompass a variation of 10% around the stated value.

Fermentation of *E. coli* K5 for the Production of Heparosan

Many factors must be considered in the identification of appropriate conditions for fermentation.

*E. coli*, in general, can grow in a wide variety of media and a range of pH, temperature, $O_2$ and other condition. Unlike laboratory adapted strains, however, *E. coli* K5 has not been subjected to extensive study of genetics, growth, and function.

Variations in the growth conditions can affect (a) the rate of bacterial growth, (b) maximal cell density, (c) production of the K5 exopolysaccharide capsule, (d) the degree of modification of the K5 capsule by *E. coli* K5, bacteriophage resident within *E. coli* K5, and other factors, (e) the release of the K5 exopolysaccharide capsule into medium, (f) whether the heparosan polysaccharide produced is of a size range suitable for processing into heparin, and (g) the amount and type of contaminants. For example, conditions that promote cell lysis may increase the yield of the K5 exopolysaccharide in the culture supernatant, but may also increase the degradation the K5 exopolysaccharide capsule and the number and amount of contaminants in the supernatant.

The importance of any one contaminant is related to the ease by which it may be removed by subsequent purification and processing steps, whether the contaminant interferes with subsequent processing of heparosan into heparin, and whether the contaminant poses a danger to humans or animals. *E. coli* K5 is a known pathogen, and thus toxins and other virulence-related factors must be removed. Lipolysaccharide (LPS) is a common contaminant of Gram negative bacterial extracts, and is known to be a potent immunostimulant and toxin. Nucleic acids may also be immunostimulatory. Both LPS and nucleic acids have polysaccharide cores, and so may co-purify with heparosan. Other contaminants may include non-heparosan polysaccharides or derivatives of heparosan.

For the production of pharmaceutical and medical products, the source and nature of the growth medium may be important. For example, complex media obtained by the hydrolysis of animal or plant proteins is excellent for the growth and production of *E. coli* K5, but shows variation between batches and may contain antigenic and other contaminants.

Additional factors must be considered for production of heparosan on an industrial scale including culture volume, time, and temperature of fermentation. Smaller volumes of medium, and faster growth conditions are therefore desirable. Also relevant is the identification of a growth medium that uses widely available, standardized and inexpensive starting materials.

Growth conditions must also be demonstrated to be scalable. Thus, the identification of an optimal condition in a 5 ml culture must also be demonstrated in larger scales, such as 5 L, 20 L, 100 L, and more. Relatedly, the process should be robust and reproducible, and therefore not susceptible to small changes in conditions.

In view of the foregoing, the identification of conditions suitable for the industrial production of heparosan are non trivial. The present inventors have identified suitable growth and culture conditions for *E. coli* K5 to facilitate the production, isolation and purification of heparosan, which are adaptable to industrial production.

The media are defined media with glucose as the carbon source, which is varied depending on the growth phase. The composition of the medium for the batch growth is as the following per liter: about 20 g glucose, 10-300 mg thiamine, about 13.5 g $KH_2PO_4$; about 4.0 g $(NH_4)_2HPO_4$, about 1.4 g $MgSO_4.7H_2O$, about 1.7 g citric acid, and about 10.0 mL trace metal solution. The trace metal solution consisted of (per L of 5M HCl) 10.0 g $FeSO_4.7H_2O$, 2.0 g $CaCl_2$, 2.2 g $ZnSO_4.7H_2O$, 0.5 g $MnSO_4.4H_2O$, 1.0 g $CuSO_4.5H_2O$, 0.1 g $(NH_4)_6Mo_7O_{24}.4H_2O$, and 0.02 g $Na_2B_4O_7.10H_2O$. The feeding solution during the fed batch cultures consisted of (per L): 250-1000 g glucose, 20 g MgSO$_4$.7H$_2$O and 0.15-0.5 g thiamine, and may be further supplemented with 47 g KH$_2$PO$_4$. In some embodiments, the feeding solution was 700 g glucose, 20 g MgSO$_4$.7H$_2$O and 0.2 g thiamine. In another embodiment, the feeding solution was 700 g glucose, 20 g MgSO$_4$.7H$_2$O, 47 g KH$_2$PO$_4$ and 0.4 g thiamine.

A seed culture was prepared by growing *E. coli* K5 strain overnight at 37° C. in a conical flask. The seed culture is then inoculated into a fermentor. The fermentation in the fermentor consists of two phases: a batch growth phase, and a phase that utilizes a combination of exponential feeding and DO-stat feeding strategies. The batch growth phase starts after the seed culture is inoculated in the fermentor. The temperature is kept at around 37° C., and pH is kept between 6 and 8 by adding NH$_4$OH as pH goes down.

The second fermentation phase starts after the dissolved oxygen shows a sharp increase and glucose in the medium is depleted. The feeding rate of the glucose is calculated generally according to the equation but with flexibility $$M_s(t) = F(t)S_F(t) = \left(\frac{\mu}{Y_{X/S}} + m\right)X(t)V(t) = \left(\frac{\mu}{Y_{X/S}} + m\right)X(t_0)V(t_0)\exp[\mu(t-t_0)]$$

where: Ms Mass-flow rate of the carbon source (g/h); F Feed flow rate (l/h); SF Carbon substrate concentration in the feed (g/l); X Cell concentration (g/l dcw); m Specific maintenance coefficient (g/g dcw/h); V Culture volume (l); t0 Time of feeding start; t Process time; µ Specific growth rate (l/h); YX/S Cell yield on carbon substrate (g/g).

During the whole feeding process, µ is set between 0.1-0.4.

In some embodiments, there may be pauses during the feeding as checkpoints to ensure the glucose is not over-fed and the toxic substance such as acetate in the culture medium is low. In these checkpoints, the feeding is resumed after a sharply increase of the dissolved oxygen concentration is observed, which indicates the depletion of the glucose in the culture medium. In larger scale, such observations are made continuously with probes, or with automatic sampling and analysis during fermentation.

Typically, the fermentation continues until no increase in the cell density is observed. The feeding is then stopped and the stirrer of the fermentor is left on for 30-60 minutes more to shear more capsule K5 polysaccharide off the cell surface and into the medium.

Purification of Heparosan from Fermentation Culture

In one exemplary embodiment, the heparosan purification may comprise (a) a step to prepare a culture supernatant or filtrate, (b) binding of heparosan to a solid phase, such as a resin, and elution of the heparosan therefrom; (c) precipitation with alcohol and (d) depyrogenation. Additional binding, precipitation and depyrogenation steps may be added.

In step (a), the culture is centrifuged or filtered to separate the supernatant from the cell pellet. Formalin or other agents may be added to the culture to inactivate the bacteria cells. Typically, heparosan is recovered from the supernatant, but may also be recovered by washing the cells, including with a detergent such as sodium dodecyl sulfate and mechanical agitation, followed by pelleting and extraction of heparosan from the supernatant.

In step (b) the heparosan is bound to a solid phase that preferentially binds heparosan. For example a resin, such as an anion exchange resin, is added to the supernatant from step (a). The mixture is agitated to bind the heparosan in the supernatant onto the resin. The mixture is then filtered to separate the resin from the solution. The separated solid is then washed to rinse unbound contaminants and eluted.

For anion exchange resins, this would include washing with low salt concentration solution to rinse unbound contaminants, and elution with 1-2 M sodium chloride solution. Chitosan may also be used to bind heparosan. While chitosan may be added as a solution, and is therefore not in a "solid phase," it precipitates out and thereby carries heparosan from the supernatant. Similarly, heparosan could be run through an appropriate column containing a solid phase, washed and eluted.

In step (c), the resulting heparosan eluate from step (b) is precipitated, such as by adding 1-5 parts by volume of ethanol or methanol. This step not only concentrates the heparosan but selectively removes contaminants. The precipitate is then separated by centrifuge and washed with 50-80% alcohol.

In step (d), the precipitate is dissolved in water, and subjected to a depyrogenation step to inactivate remaining lipopolysaccharide and other contaminants. Typically this is performed with an oxidizing agent such as hydrogen peroxide, but other peroxides or bleaching agents are known. The resulting heparosan is precipitated again, as above, and dried.

Analysis

The resulting heparosan is analyzed to determine the yield, purity and suitability for further processing. Several analytical tools may be used.

The disaccharide composition may be analyzed with high performance liquid chromatography (HPLC)-electrospray ionization (ESI)-mass spectrometry (MS) after partial digestion of the heparosan. Bhattacharyya S et al. (2010) "Cell-bound IL-8 increases in bronchial epithelial cells after arylsulfatase B silencing due to sequestration with chondroitin-4-sulfate," *Am J Respir Cell and Molec Biol* 42, 51-61. $^1$H-NMR and $^{13}$C-NMR can also be used on undigested heparosan and is suitable for determining the concentration and purity of heparosan. Wang Z, Zhang Z, McCallum S A, Linhardt R J. 2009. Nuclear magnetic resonance quantification for monitoring heparosan K5 capsular polysaccharide production. Anal Biochem. 398(2):275-7. Heparosan can also be determined with carbazole analysis as reported by Bitter T, Muir H M. (1962) "A Modified Uronic Acid Carbazole Reaction." *Analytical Biochemistry* 4(4):330

DNA content may be determined by UV absorbance. Protein content may be determined with, well known kits, such as the Micro BCA Protein Assay Kit following manufacturer's instructions.

The molecular weight profile of purified heparosan is determined by comparison with a ladder of known molecular weights of heparosan or hyluronic acid, and used to calculate the molecular weight average, number, and distribution.

Pyrogen content may be determined with the limulus amoebocyte lysate (LAL) assay.

The invention may be further understood by reference to the following examples, which are provided to illustrate certain embodiments of the invention are not intended to be limiting. The person of ordinary skill would understand that variations may be made without departing from the spirit of the invention.

EXAMPLES

Example 1

Materials

A 7-L glass autoclavable bioreactor from Applikon (Schiedam, Netherlands) was used as the fermentor. BioXpert V1.5 software was used to control fermentor operation and collect data. Difco™ LB broth powder was purchased from BD (Franklin Lakes, N.J.). Most of the chemicals used for preparing the synthetic media were from Sigma-Aldrich (St Louis, Mo.). Antifoam 204 was from Sigma-Aldrich (St Louis, Mo.). Baffled shake flasks are from Corning (Corning, N.Y.). DEAE Sepharose Fast Flow from GE Healthcare (Piscataway, N.J.) was used for the purification of heparosan. Vivapure D Mini H spin columns were from Sartorius Stedim Biotech (Aubagne, France). Micro BCA Protein Assay Kit was from Thermo Scientific (Rockford, Ill.). The enzymes used to digest the heparosan for disaccharide analysis were expressed and purified in our lab as described in Han et al. (2009) "Structural snapshots of heparin depolymerization by heparin lyase I" *J Biol Chem* 284(49):34019-27. HPLC-MS was performed on an Agilent 1100 instrument (Santa Clara, Calif.). TLC silica gel plates were from EMD (Gibbstown, N.J.). The materials for preparing the heparosan MW ladder and determining heparosan $M_w$ were described in detail in Ly M, et al (2010) "Analysis of *E. coli* K5 capsular polysaccharide heparosan" *Anal Bioanal Chem* (DOI: 10.1007/s00216-010-3679-7). Select HAT™ LoLadder, a set of hyaluronan molecular markers, were obtained from Hyalose (Oklahoma City, Okla.).

E. coli K5 Growth in 2.8 L Shake Flasks

*E. coli* K5 from American Type Culture Collection (ATCC #23506) was stored frozen in 1 mL of M9, LB, glycerol and glucose media, with 25% glycerol. A 250 mL shake flask containing 25 mL of the same media was inoculated with 0.5 mL of defrosted *E. coli*. The culture was harvested in late exponential growth at approximately 1.1 g dry cell weight (DCW)/L for M9 medium culture, 5.4 g DCW/L for glycerol synthetic medium, 5.6 g DCW/L for glucose synthetic medium, and 1.9 g DCW/L for LB medium. *E. coli* K5 culture (300 mL) was next grown in 2.8 L shake flasks inoculated with 5 vol % cells in late exponential growth. The culture was shaken at 220 RPM and 37° C. until 1-4 h after growth reached stationary phase and then harvested for recovery of heparosan. The media used in 2.8 L shake flask fermentation included: 1. LB medium: Difco™ LB broth, Lennox, 20 g/L. 2. M9 medium: 2 g/L glucose, 0.12 g/L $MgSO_4$, 0.011 g/L $CaCl_2$, 0.337 g/L thiamine-HCl, 6 g/L $Na_2HPO_4$, 3 g/L $KH_2PO_4$, 0.5 g/L NaCl, 1 g/L $NH_4Cl$. 3. Glycerol defined medium: 20 g/L glycerol, 20 mg/L thiamine, 13.5 g $KH_2PO_4$; 4.0 g $(NH_4)_2HPO_4$, 1.4 g $MgSO_4.7H_2O$, 1.7 g citric acid, and 10.0 mL trace metal solution. Trace metal solution consisted of (per L of 5 M HCl) 10.0 g $FeSO_4.7H_2O$, 2.0 g $CaCl_2$, 2.2 g $ZnSO_4.7H_2O$, 0.5 g $MnSO_4.4H_2O$, 1.0 g $CuSO_4.5H_2O$, 0.1 g $(NH_4)_6Mo_7O_{24}.4H_2O$, and 0.02 g $Na_2B_4O_7.10H_2O$ Wang F L, Lee S Y (1998) "High cell density culture of metabolically engineered *Escherichia coli* for the production of poly(3-hydroxybutyrate) in a defined medium" *Biotechnology and Bioengineering* 58(2-3):325-328. 4. Glucose defined medium: per liter 20 g glucose, 20 mg thiamine, 13.5 g $KH_2PO_4$; 4.0 g $(NH_4)_2HPO_4$, 1.4 g $MgSO_4.7H_2O$, 1.7 g citric acid, and 10.0 mL trace metal solution. Trace metal solution consisted of (per L of 5 M HCl) 10.0 g $FeSO_4.7H_2O$, 2.0 g $CaCl_2$, 2.2 g $ZnSO_4.7H_2O$, 0.5 g $MnSO_4.4H_2O$, 1.0 g $CuSO_4.5H_2O$, 0.1 g $(NH_4)_6Mo_7O_{24}.4H_2O$, and 0.02 g $Na_2B_4O_7.10H_2O$ Wang and Lee (1998), id.

E. coli K5 Growth in a 7 L Fermentor

This fermentation consists of a batch growth stage and a fed batch growth stage. The composition of the medium for the batch growth in the fermentation was: (per liter) 20 g glucose, 20 mg thiamine, 13.5 g $KH_2PO_4$; 4.0 g $(NH_4)_2HPO_4$, 1.4 g $MgSO_4.7H_2O$, 1.7 g citric acid, and 10.0 mL trace metal solution. Trace metal solution consisted of (per L of 5 M HCl) 10.0 g $FeSO_4.7H_2O$, 2.0 g $CaCl_2$, 2.2 g $ZnSO_4.7H_2O$, 0.5 g $MnSO_4.4H_2O$, 1.0 g $CuSO_4.5H_2O$, 0.1 g $(NH_4)_6Mo_7O_{24}.4H_2O$, and 0.02 g $Na_2B_4O_7.10H_2O$. The feeding solution used in the fed batch stage consisted of (per L): 700 g glucose, 20 g $MgSO_4.7H_2O$ and 0.2 g thiamine. Wang and Lee (1998), id.

The batch growth stage began with the inoculation of seed culture (300 mL of 5.6 g/L DCW) obtained from a shake flask in late exponential growth. The temperature was maintained at ~37° C., and the pH was maintained at approximately 7 (by adding 29% ammonia solution). Air was sparged into the fermentor to supply oxygen, and the stirrer speed was set to 520 RPM.

The second stage of the fermentation began after glucose in the batch growth medium had been depleted and the dissolved oxygen showed a sharp increase. The feeding solution was then fed exponentially following Eq. 1:

$$Ms(t) = F(t)s_{F(t)} = \left(\frac{\mu}{Y_{\frac{x}{s}}} + m\right)X(t_0)V(t_0)\exp[\mu(t - t_0)] \quad (1)$$

Ms is mass flow rate of the carbon source (g/h); F is feed flow rate (L/h); $S_F$ is carbon substrate concentration in the feed (g/L); X is cell concentration (g/L dcw); m is specific maintenance coefficient (g/g dcw/h); V is culture volume (L); $t_0$ is time of feeding start; t is process time; μ is specific growth rate ($h^{-1}$); and $Y_{x/s}$ is cell yield on carbon substrate (g/g) Lee S Y. 1996. "High cell-density culture of *Escherichia coli*". *Trends Biotechnol* 14(3):98-105. A μ value between 0.10-0.15 $h^{-1}$ was used in this study to allow sufficient cell propagation while avoiding accumulation of toxic side products due to higher growth rates. The "acid pump" attached to the fermentor was used to carry out the glucose feeding function instead of adding real acid, and the base pump was used to add 29% ammonia solution to maintain stable pH and provide the culture with a nitrogen source. A third pump was used to add the Antifoam 204 reagent into the culture when foaming exceeded a set level controlled by the feedback loop through the digital control unit of the fermentor. Glucose-feeding rate was achieved by programming the "acid pump" on-off time for one-minute. An equation of $T_{on}=0.72*\exp[0.0023*(t-420)]$ was used between 7 h and 24 h of elapsed fermentation time, where $T_{on}$ is the time the "acid pump" was turned on for one second during the one-minute period. The glucose-feeding rate was decreased after 24 h once oxygen limitation was observed. pH control was achieved manually using a base pump to add 29% ammonium hydroxide solution. The pH was more closely controlled using a customized program written into the BioXpert V1.5 software. The stirrer speed and/or airflow rate were increased when dissolved oxygen dropped below 20% air saturation. Pure oxygen was mixed with air to afford sufficient dissolved oxygen after 24 h of fermentation time. Glucose feeding was periodically halted to assure that the cells consumed all the glucose, and that toxic byproducts (such as acetate) did not build up in the medium. Feeding was resumed after a spike of dissolved oxygen was observed, indicating the depletion of glucose and the formation of toxic by products. Johnston W A, et al. (2003) "Tracking the acetate threshold using DO-transient control during medium and high cell density cultivation of recombinant *Escherichia coli* in complex media" *Biotechnol Bioeng* 84(3): 314-23. Samples were collected from the fermentor periodically. The samples taken were centrifuged at 12,000×g for 30 min. to separate the supernatant from the *E. coli* cells.

Determination of Heparosan Concentration in the Fermentation Supernatant

The heparosan concentration in the fermentation supernatant was measured by both carbazole analysis and NMR analysis. In the carbazole assay of heparosan, 0.5 mL of fermentation supernatant recovered by centrifugation was applied to a Millipore YM-3 desalting spin column (1200×g) to remove salts and small molecules. The retentate containing crude heparosan was recovered and lyophilized. The dried crude heparosan was reconstituted with 0.5 mL of distilled water and subjected to the carbazole assay. The concentration of heparosan was calculated from a standard curve prepared using pure heparosan. In the NMR assay, heparosan (1 mL), similarly recovered from culture supernatant, was lyophilized and then dissolved in 400 µL of $D_2O$ containing 71 µg of sodium terephthalate (internal standard) then transferred to an NMR tube for $^1$H-NMR at 600 $MHz$. The concentration of heparosan was calculated from the ratio of the integrated area of the N-acetyl group in heparosan and that of the internal standard.

Rapid Recovery of Heparosan Samples During Fermentation for Analysis

Heparosan was rapidly recovered from fermentation supernatant and partially purified using a Vivapure D Mini H spin column. Supernatant (1 mL), recovered from cells by centrifugation (12,000×g), was mixed with 1 mL of buffer A (50 mM sodium chloride, 20 mM sodium acetate, pH 4). The mixture was then adjusted to pH 4 and loaded onto a pre-equilibrated Vivapure D Mini H column. The column was then washed with buffer A and eluted with buffer B (1 M sodium chloride, 20 mM sodium acetate, pH 4). Eluted samples were then precipitated with 3 volumes of ethanol left overnight at −20° C. (in an explosion-proof freezer) and the resulting precipitate washed with 75% ethanol, dissolved in water and lyophilized. The purity of the recovered samples was then examined by $^1$H-NMR.

Purification of Heparosan

Heparosan was recovered at the completion of fermentation in either a shake flask or the 7-L fermentor by centrifuging the culture at 12,000×g for 30 min. The supernatant obtained was adjusted to pH 4 by adding glacial acetic acid and then filtered through a Pyrex Buchner funnel with a fritted disc (pore size 40-60 µm). DEAE-Sepharose fast flow resin was packed into a column of the appropriate size (<20 mg of heparosan/mL of swelled resin). The column was first equilibrated with 50 mM sodium chloride in 20 mM sodium acetate buffer at pH 4. The fermentation supernatant was then loaded onto the column and the column was washed with 3-volumes of 50 mM sodium chloride in 20 mM sodium acetate buffer at pH 4. Heparosan was then eluted from the column with 1 M sodium chloride in 20 mM sodium acetate buffer at pH 4. The heparosan that eluted from the column was precipitated by adding 3-volumes of ethanol and storing this solution overnight at −20° C. in an explosion-proof freezer. The precipitate was recovered by centrifuging at 12,000 g for 30 min. The pellet was washed with 75% ethanol, centrifuged again and the pellet obtained was either lyophilized for storage or used directly for the bleaching step. Heparosan could also be purified from the cell pellet by addition of 0.02% SDS followed by vigorous stirring, centrifugation and DEAE chromatography.

In the bleaching step, heparosan was first dissolved in 1 M sodium chloride at a concentration of ~15 g/L. The pH of the solution was adjusted to 9.5 with 1 M NaOH and hydrogen peroxide (30%) was added to obtain a final concentration of 1.5%. The mixture was incubated overnight at room temperature, after which the heparosan was precipitated by adding 3-volumes ethanol and left overnight at −20° C. (in an explosion-proof freezer). The resulting pellet was washed with 75% ethanol, dissolved in water and dried.

Disaccharide Analysis of Heparosan

Heparosan (10 mg/mL) was dissolved in 200 mM sodium phosphate buffer at pH 7 and treated with 1 mU each of heparin lyase 1, 2 and 3 at 30° C. overnight. The resulting disaccharide product was subjected to high performance liquid chromatography (HPLC)-electrospray ionization (ESI)-mass spectrometry (MS) on an Agilent Ion trap instrument and the disaccharide composition was determined. LC-MS analysis was performed on an LC-MS system (LC/MSD trap MS; Agilent, Santa Clara, Calif.). Solutions A and B for high-pressure liquid chromatography were 15% and 65% acetonitrile, respectively, containing the same concentration of 37.5 mM $NH_4HCO_3$ and 11.25 mM tributylamine. The separation was performed on a C-18 column (Agilent) using solution A for 20 min, followed by a linear gradient from 20 to 45 min of 0-50% solution B. The column effluent entered the source of the electrospray ionization mass spectrometry (ESI-MS), for continuous detection by MS. The electrospray interface was set in negative ionization mode with skimmer potential of 400 V, capillary exit of 240.0 V, and a source of temperature of 325° C., to obtain maximum abundance of the ions in a full-scan spectrum (150-1,500 Da, 10 full scans/s). Nitrogen was used as a drying (5 liters/min) and nebulizing gas (20 psi). Bhattacharyya S, *Am J Respir Cell and Molec Biol* 42, 51-61.

NMR Analysis of Heparosan $^1$H-NMR and $^{13}$C-NMR were conducted on a Bruker 600 MHz NMR spectrometer. The heparosan samples were prepared at a concentration of 2 mg/mL in $D_2O$ (99.99+ atom %), freeze-dried to remove exchangeable protons and re-dissolved in $D_2O$ and transferred to standard 5 mm NMR tubes. Acquisition of spectra was carried out using TOPSPIN 2.0 software. All the spectra were acquired at the temperature of 298 K.

DNA and Protein Content Assay

The DNA content in the final heparosan product was determined by measuring the UV absorbance of 0.1 mg/mL heparosan solution at 260 nm and 320 nm. The DNA concentration was calculated as concentration (µg/mL)=($A_{260}$ reading−$A_{320}$ reading)×dilution factor×50 µg/mL. Protein content was assayed using the Micro BCA Protein Assay Kit following manufacturer's instructions.

Analysis of the Molecular Weight of Heparosan

A ladder of heparosan standards of known molecular masses, was prepared from bleached K5 heparosan polysaccharide by continuous preparative polyacrylamide electrophoresis using a Mini Prep Cell (Biorad, Hercules, Calif.) apparatus (Ly et al., 2010). Heparosan fractions were characterized by Fourier transform-mass spectrometry (FT-MS) and remixed to prepare a ladder of molecular weight standards for the determination of the molecular weight properties of heparosan (Ly et al., 2010). Molecular markers of hyaluronan (HA), which is also linear polysaccharide with the same charge density as N-acetylheparosan, were used as standards for the upper range of samples.

Both HA and heparosan molecular markers were used as a set of standards for the molecular weight analysis of the heparosans prepared in different culture media and at different fermentation time points. A gradient polyacrylamide gel (4-15%) of dimensions 0.75 mm×6.8 cm×8.6 cm was used in heparosan molecular weight analyses. Heparosan samples (25 µg) were loaded onto gels and were then subjected to electrophoresis (200 V for 20 min) and stained with Alcian blue for 1 h, and then destained with 25% ethanol/10% acetic acid (Ly et al., 2010). The gels were scanned and these digital images were analyzed using the computer software UN-SCANIT. A plot of image density as a function of migration distance was acquired. From these data, the molecular weight properties of the heparosan samples were characterized from the standard curve obtained.

Results

*E. coli* K5 Fermentation in Shake Flasks for the Preparation of Heparosan

Figure 2:
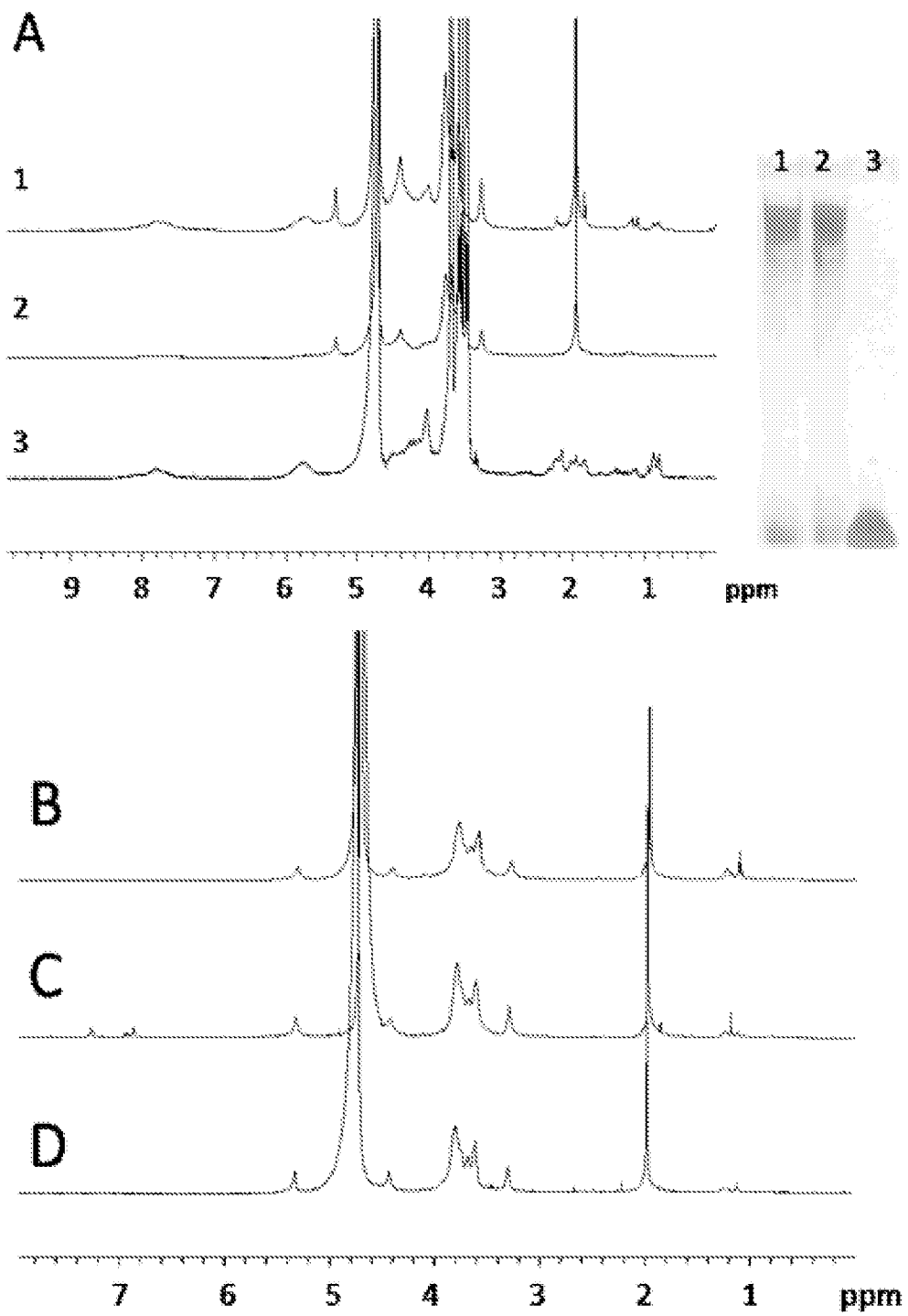
FIG. 2. $^1$H-NMR spectra (600 MHz) of heparosan prepared in shake flask culture. A. stack plot of heparosan recovered from: 1. LB medium, 2. LB medium having $MW_{Avg}$>3,000, 3. LB medium having $MW_{Avg}$<3,000, and inset showing PAGE analysis of samples 1, 2 and 3. B. heparosan recovered from M9 medium. C. heparosan recovered from glycerol defined medium. D. heparosan recovered from glucose defined medium.

*E. coli* K5 was grown in shake flasks until 1-4 h after stationary phase was reached. The fermentation was extended beyond stationary phase to accumulate the maximum amount of heparosan in the medium, consistent with reports that heparosan appearance in the medium lags cell growth Manzoni M et al. (1993) *Journal of Bioactive and Compatible Polymers* 8(3):251-257. The yield of heparosan from the flask cultures ranged from 70-500 mg/L. The purity of the heparosan recovered from flask cultures was in all cases >85% as estimated by NMR Wang Z et al (2009) Anal Biochem. 398 (2):275-7. Zhang Z Q et al (2008) "Solution structures of chemoenzymatically synthesized heparin and its precursors" *Journal of the American Chemical Society* 130(39):12998-13007. The heparosan recovered from synthetic media, including M9 medium, glucose medium and glycerol medium, showed higher purity levels (>95%) than heparosan recovered from LB medium, which showed additional peaks in the NMR, consistent with ~85% purity (FIG. 2). Further analysis of the LB medium derived heparosan by polyacrylamide gel electrophoresis (PAGE) showed a low $M_W$ band, corresponding to a medium component that co-purifies with heparosan. This impurity can be removed using a 3K molecular weight cut-off (MWCO) spin column (FIG. 2A).

The disaccharide composition of heparosan was determined by HPLC-MS (not shown) following the complete digestion with heparin lyase 1, 2 and 3, and showed the presence of a single disaccharide m/z 378.2. This disaccharide corresponds to ΔUA(1→4)-α-D-GlcNAc, is consistent with the uniform repeating structure of heparosan, →4)-β-D-GlcA (1→4)-α-D-GlcNAc (1→. To confirm this structure $^{13}C'$ and $^{15}N'$ labeled heparosan was prepared by culturing the *E. coli* K5 in M9 medium containing uniformly labeled $^{13}C$-glucose and $^{15}N$-ammonium chloride. The structure of the recovered uniformly labeled $^{13}C$-, $^{15}N$-heparosan was confirmed by complete digestion with heparin lyase 1, 2 and 3 followed by HPLC-MS, which showed a single disaccharide m/z 392.9. The 15 amu difference between m/z 378.2 and 392.9 is consistent with the full $^{13}C$ and $^{15}N$ isotopic enrichment of heparosan and confirms the heparosan repeating structure.

*E. coli* K5 Fermentation in a 7 L Fermentor

Figure 3:
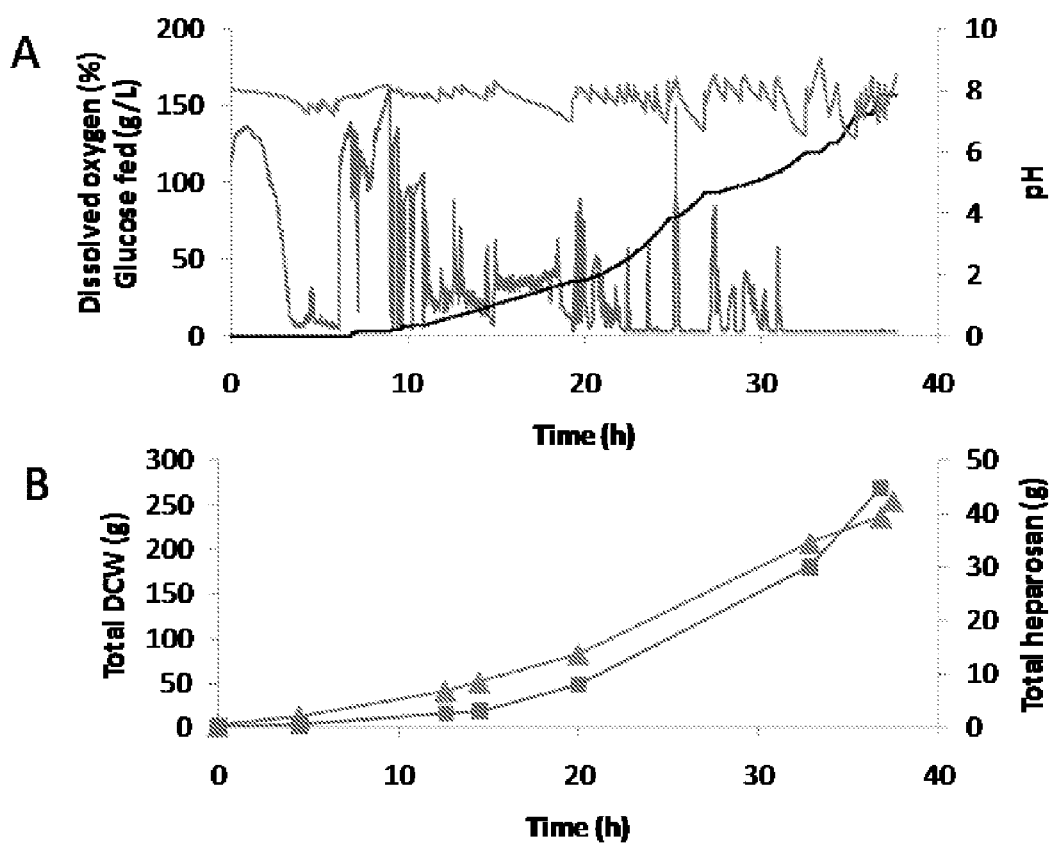
FIG. 3. Production of heparosan in a 7 L fermentor. Panel A shows the glucose feed curve (black), the pH curve (blue) and the dissolved oxygen (% DO) curve (red) as a function of fermentation time (h). Panel B shows the cell growth curve (total DCW g, ▲) and heparosan production (g, ■) as a function of fermentation time (h).

The feeding rate was exponentially increased to keep up with the exponential growth of *E. coli*. Several pauses were made in the feeding stage to ensure that there was no buildup of glucose in the medium, which could result in acetate accumulation and inhibit *E. coli* growth. The feeding was resumed only after an increase in dissolved oxygen was observed confirming the depletion of glucose (FIG. 3). In the late stages of the fermentation (after 22 h), dissolved oxygen became limiting. Increased agitation and the introduction of pure oxygen were used to maximize the dissolved oxygen concentration in the culture. Despite these efforts the dissolved oxygen levels still remained quite low after 31 h. The glucose-feeding rate was decreased when oxygen became the limiting nutrient. Throughout the fermentation, the pH was maintained between 6 and 8 by adding NH$_4$OH. After 37.5 h fermentation, a cell density of 85 g DCW/L was reached, and the heparosan concentration in the fermentation supernatant was determined to be 15 g/L. An overall growth rate was calculated to be 0.12 h$^{-1}$, the overall production rate was 1.2 g/h, and the volumetric production rate was 0.4 g/L·h. The heparosan purified from the fermentation was of high purity, judging from the $^1$H-NMR spectrum (FIG. 4A). Additionally, DNA and BCA protein assays indicated that <1% DNA and <2% protein were present in the final heparosan material.

Figure 4:
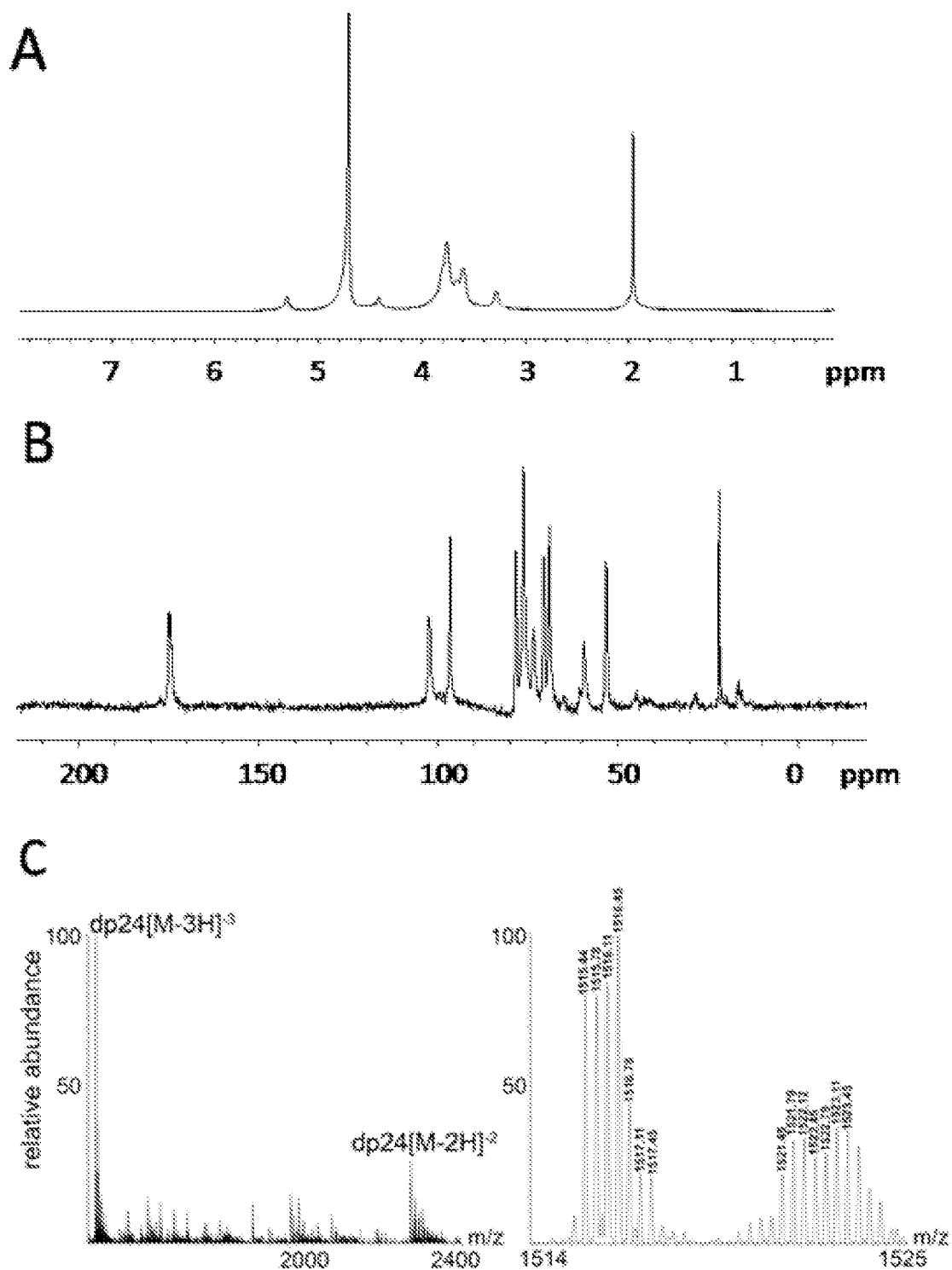
FIG. 4. Characterization of heparosan purified from the supernatant of a 7 L fermentation. A. $^1$H-NMR (600 MHz) of heparosan. B. $^{13}$C-NMR of heparosan prepared on M9 medium containing $^{13}$C glucose and $^{15}$N ammonia sulfate. C. FT-MS of a heparosan chain of average molecular weight 4551.81 (degree of polymerization=24) purified by preparative PAGE (Ly et al., 2010).

Structural Characterization of Heparosan $^1$H-NMR, $^{13}$C-NMR, HPLC-MS and Fourier Transform (FT)-MS (FIG. 4) all confirm the general structure of heparosan as →4)-β-D-GlcA (1→4)-α-D-GlcNAc (1→ (FIG. 1A). FT-MS of a heparosan fraction having a degree of polymerization (dp) of 24, obtained using preparative electrophoresis is shown in FIG. 4C. This spectrum also indicates the presence of unsaturated uronate ΔUA residue (FIG. 1B) at the non-reducing end of some of the polysaccharide chains. The presence of a terminal ΔUA residue is consistent with the action of an K5 heparosan lyase also present in the *E. coli* strain K5. FT-MS analysis suggests heparosan recovered from fermentation supernatant contains a mixture of heparosan terminated with ΔUA residues and with GlcA residues. This result is consistent with some of the heparosan in the medium being shed from the cell surface by shear force and some being released into the medium by the heparosan lyase digestion. Heparosan isolated from the supernatant was treated with β-glucuronidase, an exolytic enzyme capable of removing GlcA but not DUA from the non-reducing end of a heparosan chain. The observation of released GlcA using thin layer chromatography (data not shown) confirms that some of the heparosan chains that were shed into the supernatant were terminated with GlcA.

MW Characterization of Heparosan

Figure 5:
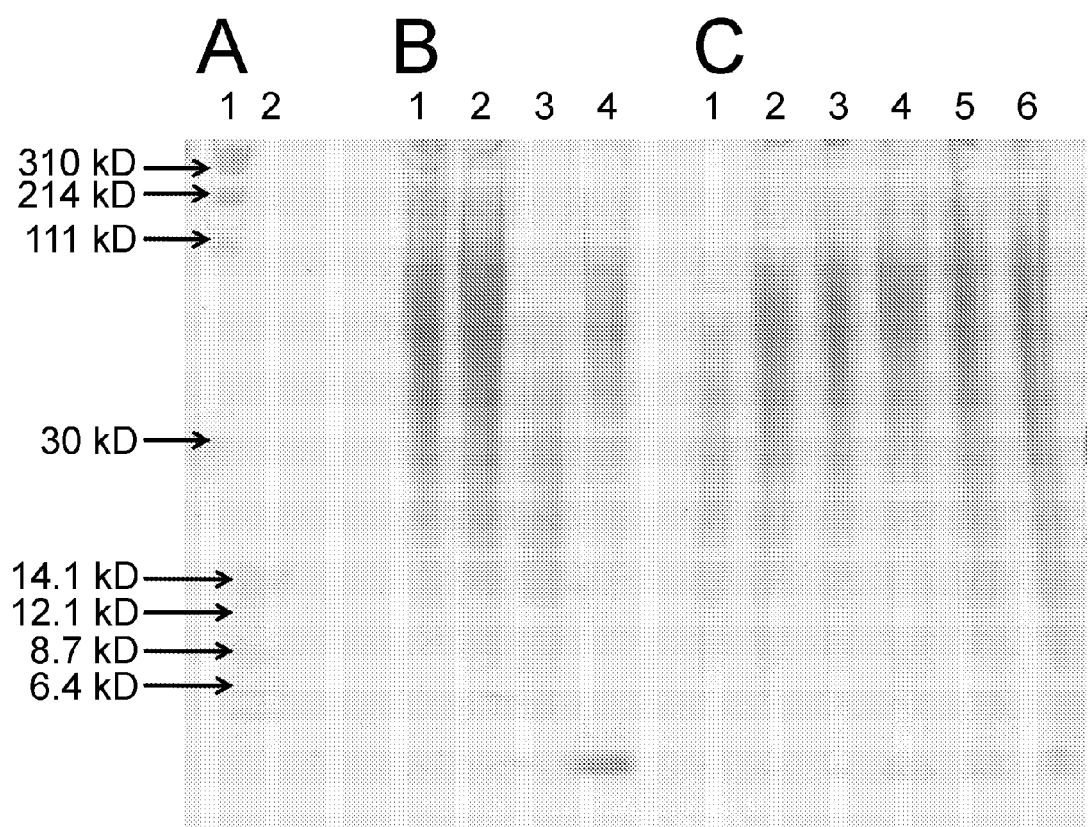
FIG. 5. PAGE used for MW analysis of heparosans with Alcian blue stain. A. molecular standards spanning the range of the gradient gel. Lanes contain: 1. HA molecular markers (30 kD-310 kD), 2. heparosan molecular markers (6.4 kD-14.1 kD). B. heparosans prepared in shake flasks in different media. Lanes contain: 1. heparosan from M9 medium, 2. heparosan from glycerol synthetic medium, 3. heparosan from glucose synthetic medium, and 4. heparosan from LB medium. C. heparosans prepared in a 7 L fermentor sampled at different times. Lanes contain: 1-6. heparosan sampled from the fermentor at 4.5 h; 12.6 h; 14.5 h; 20 h; 32.9 h; and 37.6 h after the start of the fermentation.

The heparosans recovered from *E. coli* K5 grown in shake flasks, were analyzed by PAGE against a ladder of purified heparosan standards (FIG. 5 and Table 1). Heparosan, recovered from supernatant in flask cultures grown on M9 medium, glycerol synthetic medium, LB complex medium showed little difference in $M_n$ or $M_w$. Heparosan recovered from the supernatant in glucose synthetic medium had the lowest $M_n$ and $M_w$. Heparosan recovered from the pellet showed higher $M_w$ than heparosan recovered from the fermentation supernatant (data not shown).

Figure 6:
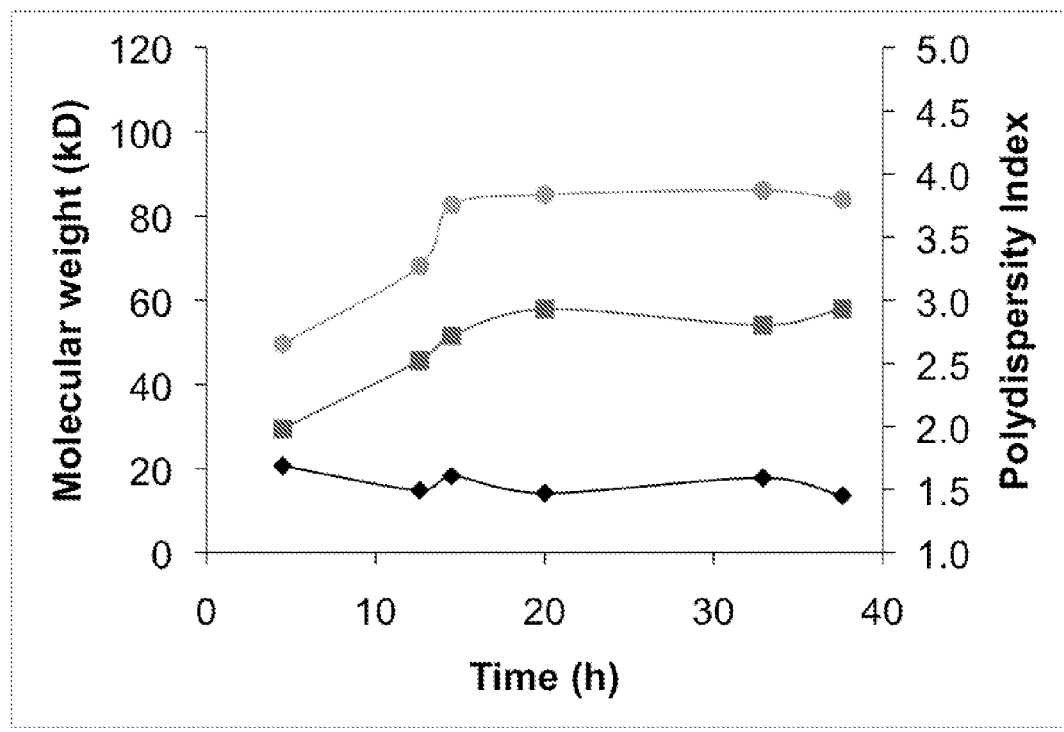
FIG. 6. Time course of molecular weight properties of heparosan produced in 7 L fermentor. Shown are the trends of $M_N$ (▨), $M_W$ (▨) and PDI (♦).

Next, samples from the fermentor were taken at various times throughout the fermentation and heparosan was purified by Vivapure D Mini H spin column. The purity of the resulting samples was confirmed to be >85% from the fermentation supernatants by $^1$H-NMR. PAGE analysis (FIG. 5B) showed an initial increase in heparosan molecular weight followed by no further changes in molecular weight as fermentation time increases (FIG. 6). Heparosan polydispersity index (PDI=$M_w/M_n$) changed little throughout the fermentation.

Discussion

In this study, a high heparosan yield in the fermentation supernatant (15 g/L) was achieved in a fed-batch fermentor culture grown on defined medium containing glucose. This compares favorably to yields recently reported of 10.2 g/L heparosan from the same organism grown on a defined media containing glycerol (US Patent Appl. Publ. No. 2008/0032349) Volumetric production rate was also increased compared to this previous report. Furthermore, glucose, as a less expensive carbon source than glycerol, makes this fermentation process more economical. The fed-batch fermentation process developed at the 3-L scale might serve as the prototype for larger lab-scale fermentation, ultimately leading to industrial heparosan production. Process scale-up studies are currently underway in our lab moving from 3 L to 750

L working volumes, which will provide the basis for scale-up to the ~100,000 L working volumes required for large-scale (100 metric ton) heparosan production to supply as the starting material for bioengineered heparin synthesis. The possibility of using a faster glucose feeding rate in the fermentation and higher oxygen levels in the fermentor is being investigated to increase the production rate the heparosan.

The use of defined media containing glucose as the carbon source has both lowered the fermentation cost and reduced media complexity, making the purification process easier. Heparosan purified from complex LB medium was less pure due to complex media components and required additional purification steps than did heparosan purified from glucose-containing defined media.

Heparosan, isolated from the culture supernatant arises from shedding into the medium during the fermentation probably through the combined actions of the K5 lyase and shear force. An increase of heparosan shedding into the media increases the yield of heparosan in the supernatant, lowering the cost of the down-steam purification process.

The presence of K5 lyase contributes to the desirable release of the heparosan capsule into the medium, increasing the heparosan yield. At the same time, the presence of the K5 heparosan lyase results in an unnatural saccharide residue, ΔUA, at the non-reducing end of the chain that may require subsequent treatment. K5 heparosan lyase also increases the polydispersity index of heparosan, which can complicate subsequent processing into heparin. The molecular weight properties of bioengineered heparin are inexorably linked to those of heparosan. The present method prepares heparosan with properties suitable for processing into heparin. Thus, the inventors have shown that in the presence of the lyase it is still possible to prepare heparosan with the desired molecular weight properties by carefully controlling the fermentation conditions and the fermentation processing time.

Future control of K5 lyase activity may offer an approach to for the fine control of heparosan controls.

TABLE 1

Number average molecular weight ($M_N$), weight average molecular weight ($M_W$) and polydispersity index (PDI) of heparosan recovered from different media in 2.8 L shake flasks.

| Medium | $M_N$ | $M_W$ | PDI |
|---|---|---|---|
| M9 | 54,000 | 82,000 | 1.5 |
| Glycerol | 50,000 | 79,000 | 1.6 |
| Glucose | 25,000 | 44,000 | 1.8 |
| LB | 54,000 | 68,000 | 1.3 |

Example 2

20 L Fermentation Report (pH Stat Fed-Batch Fermentation)

Medium

Glucose defined medium: (per liter) 20 g glucose, 20 mg thiamine, 13.5 g $KH_2PO_4$; 4.0 g $(NH_4)_2HPO_4$, 1.4 g $MgSO_4.7H_2O$, 1.7 g citric acid, and 10.0 mL trace metal solution. Trace metal solution consisted of (per L of 5 M HCl) 10.0 g $FeSO_4.7H_2O$, 2.0 g $CaCl_2$, 2.2 g $ZnSO_4.7H_2O$, 0.5 g $MnSO_4.4H_2O$, 1.0 g $CuSO_4.5H_2O$, 0.1 g $(NH_4)_6Mo_7O_{24}.4H_2O$, and 0.02 g $Na_2B_4O_7.10H_2O$. The feeding solution used in the fed batch stage consisted of (per L): 700 g glucose, 20 g $MgSO_4.7H_2O$, 47 g $KH_2PO_4$ and 0.4 g thiamine. The R medium, which is the glucose-containing medium used in the fermentations performed, was prepared as follows:

R medium Part A: $(NH_4)_2HPO_4$, $KH_2PO_4$, and citric acid were added to about 8 liters of water with magnetic stirring, trace metal solution (100× fold stock) was added, the pH adjusted to 6.80, then water added to 9 liters. Part A was sterilized in the fermentor at 121° C. for 45 minutes.

R medium Part B: $MgSO_4$ and glucose solutions made as 10× stock and sterilized separately with autoclave at 110° C. for 20 minutes (can also be filter sterilized).

Feeding solution: Glucose, $MgSO_4.7H_2O$ and 47 g $KH_2PO_4$ were dissolved in the 1 liter of water with heat and stirring, and sterilized by autoclave at 115° C. for 20 minutes. Thiamine was dissolved in water and then filter sterilized.

Operation Procedure

Day 1:

Four 5 ml culture tubes were inoculated in the glucose synthetic medium described above (R medium) with K5 *E. coli* strain (stored in −80° C. freezer) in the morning, grown in incubator at 37° C. shaking at 220 rpm for 10 hours. The four cultures were transferred to 500 ml medium in a 2.8 L baffled shake flask in the evening and grown at 37° C. shaking at 220 rpm for 10 hours.

Day 2: The fermentor pH probe and DO probe was sterilized and calibrated at growth temperature (37° C.). Three pumps were set: pump 1—$NH_4OH$ for pH adjustment; pump 2—feeding solution; pump 3—antifoam.

R medium part B was added to the fermentor to mix with part A and inoculated with the 500 ml seed culture. The pH was maintained at 6.8 by pumping in $NH_4OH$. Pumping feeding solution occurred when a pH spike and DO spike were observed. The Feeding pump was programmed to give 100% output (~6.7 g glucose pulse) when pH>6.8. The stirring speed and/or air flow rate was increased to keep the DO above 20%. A pure oxygen flow was added when the DO could not be kept at above 20% by changing stirring speed and air flow.

Day 3: The fermentation stopped when the culture's $OD^{600}$ value begins to decrease. The culture was harvested and centrifuged. Heparosan was recovered from the supernatant.

Figure 7:
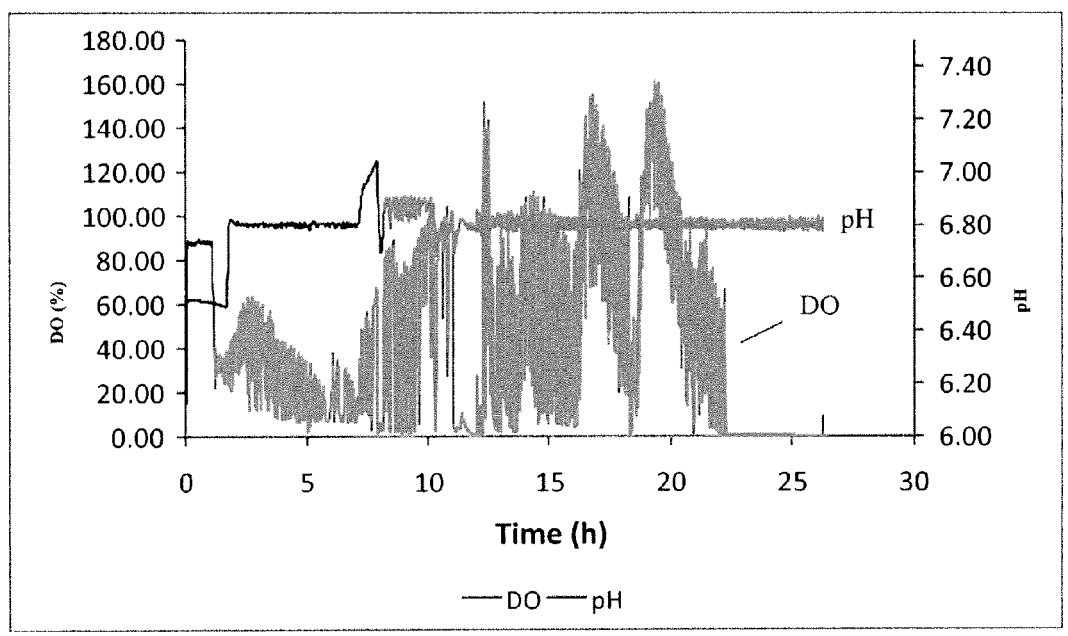
FIG. 7. The pH curve (▨) and the dissolved oxygen (% DO) curve (✴) as a function of fermentation time (h) in the 20 L fermentor.

The blue curve in FIG. 7 is the DO trend (dissolved oxygen in the culture). Because of high density of cells consumed the oxygen very rapidly, the DO went to near 0 several hours before harvesting, while the pure oxygen flow was still maintained. The fermentation was stopped a few hours after when the OD 600 (optical density of the culture at 600 nm light wavelength) began to decrease. The fermentation was stopped by turning off the oxygen flow, stopping the stirring, and then initiating harvesting.

Sampling: approx. 40 ml was taken to measure the optical density at 600 nm, then centrifuged at 12,000×g for 30 min. to separate the supernatant from the *E. coli* cells. Supernatant and cell pellet were frozen separately.

Fermentation sample analysis: dry cell weight (DCW) was measured by weighing the dried cell pellets on a scale. Heparosan concentration in the supernatant was measured by NMR quantification method or carbazole assay following ethanol precipitations Song J-M et al. (2009) "A simple method for hyaluronic acid quantification in culture broth" *Carbohydrate Polymers* 78 (2009) 633-634. Wang Z et al (2009) Anal Biochem. 398(2):275-7.

Figure 8:
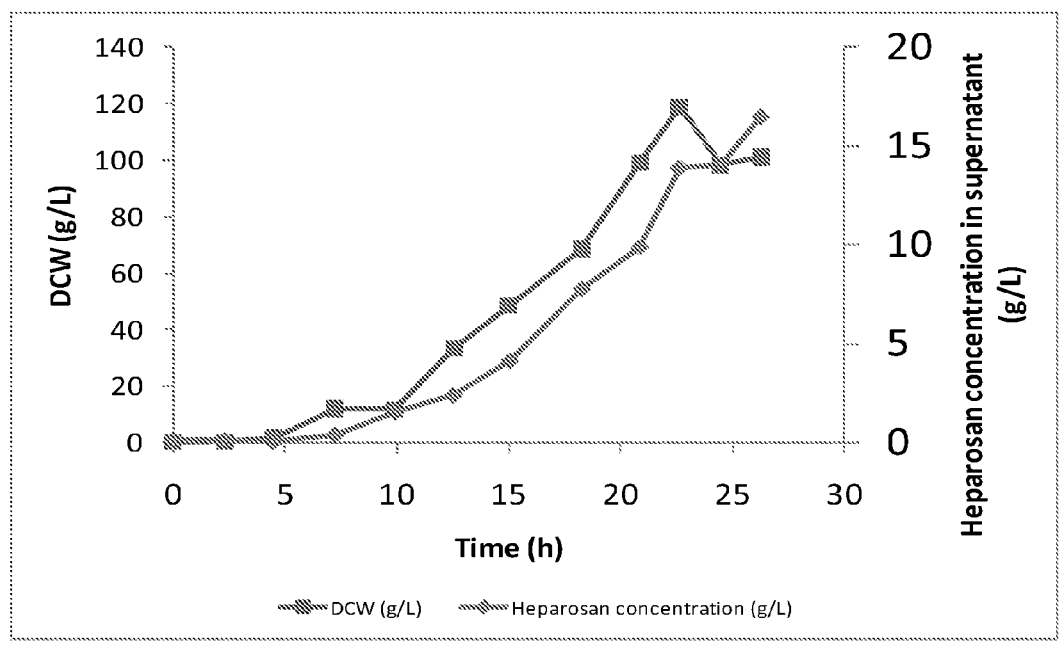
FIG. 8. The cell growth curve (DCW g/L, (▨)) and heparosan concentration in the fermentation supernatant (g/L, (✴)) time course in the 20 L fermentor.
Figure 9:
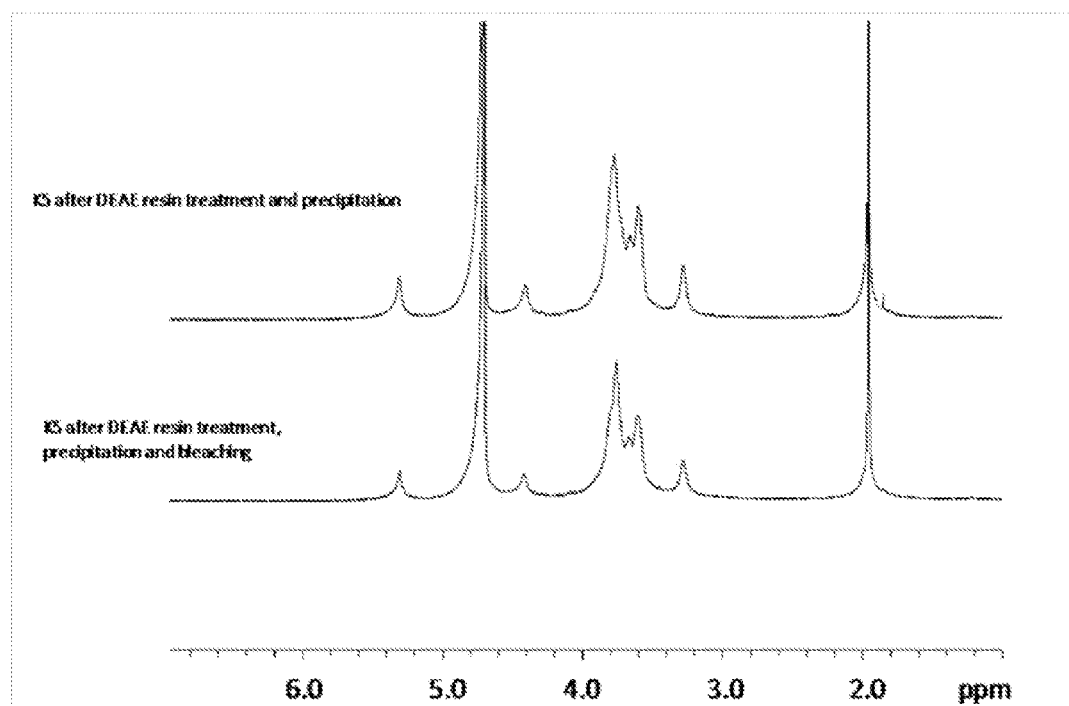
FIG. 9. $^1$H-NMR spectra of the heparosan samples purified.
Figure 10:
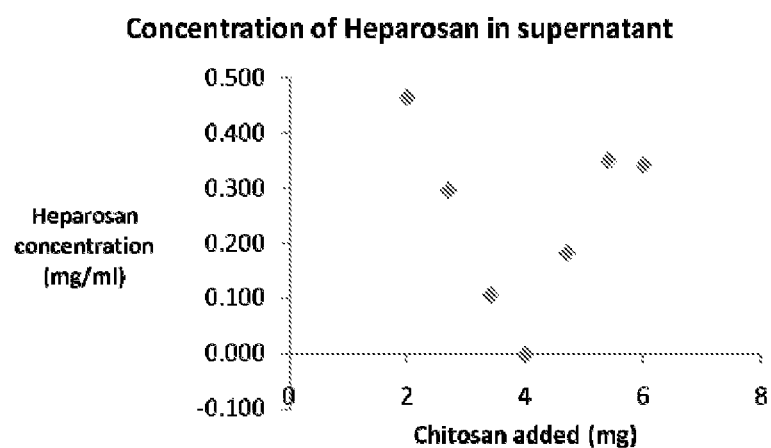
FIG. 10. Heparosan concentration in supernatant post-precipitation using varying amounts of chitosan from 10 ml of 1 mg/ml pure heparosan solution.
Figure 11:
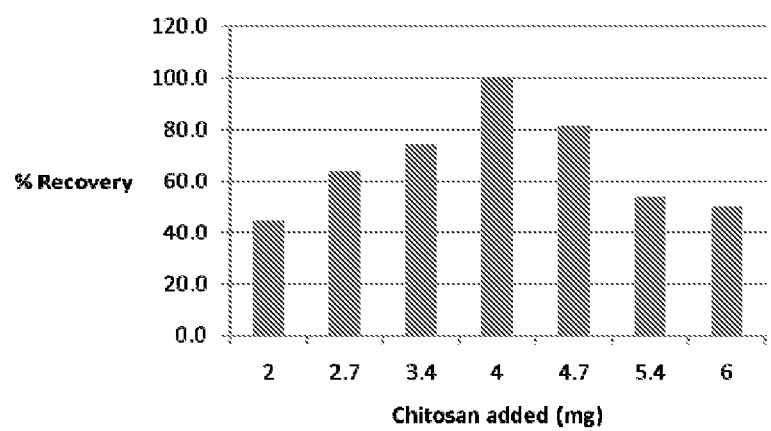
FIG. 11. Percentage recovery using varying amounts of chitosan from 10 ml of 1 mg/ml pure heparosan solution.
Figure 12:
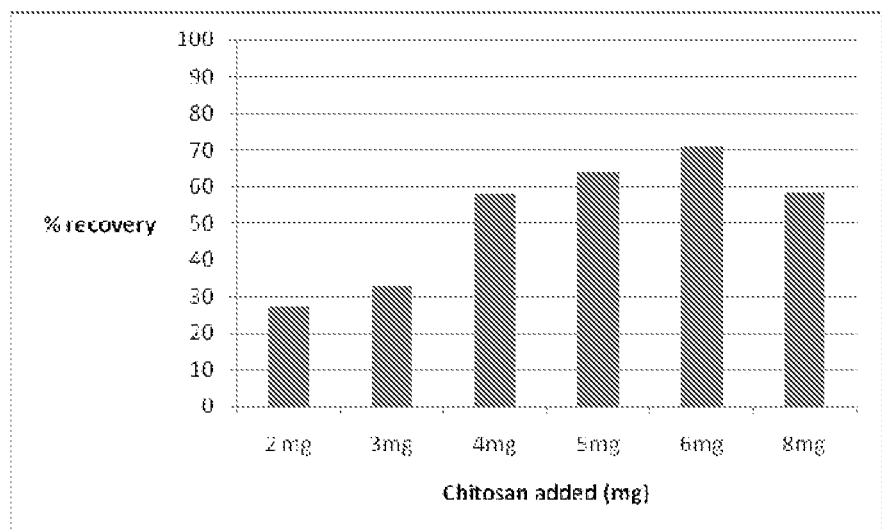
FIG. 12. Percentage recovery using varying amounts of chitosan from 10 ml of 5× diluted fermentation broth samples

The results are shown in FIGS. 7, 8 and 9.

The heparosan produced in this fermentation stage had a number average molecular weight of about 58,000 Da, a weight average molecular weight of about 84,000 Da, and polydispersity index (PDI) of about 1.4. Purity is estimated at 95% or above.

Example 3

Heparosan Purification with Chitosan Chromatography

Chitosan is a linear polysaccharide composed of randomly distributed β-(1-4)-linked D-glucosamine and N-acetyl-D-glucosamine provides for an alternative to anionic exchange resin for the chromatographic purification of heparosan. The amino group in chitosan (~pKa 6.5) makes it positively charged and soluble under acidic condition and therefore suitable for affinity based purification of negatively charged heparosan. Purification of heparosan based on chitosan can be easily controlled based on chitosan concentration and initial pH. Moreover, chitosan is inexpensive, available in abundant supply, and is biodegradable. This example describes a separation method based on soluble chitosan for efficient recovery of heparosan directly from fermentation broth. This charge neutralization based separation using chitosan potentially can be used for purification of other negatively charged macromolecules from complex fermentation mixtures.

The fermentation broth from 7 L *Escherichia coli* K5 fermentation was centrifuged at 7000 rpm for 30 min to remove the cells.

1. NMR based quantification of heparosan content in the supernatant was performed.
2. The pH of the supernatant was adjusted to 4.0 using HCl solution followed by centrifugation at 7000 rpm for 1 h to remove any impurities that precipitate out.
3. Following this the supernatant was diluted 5-fold using pH 4.0 DI water.
4. 10 mg/ml chitosan solution was prepared by dissolving chitosan in 1% acetic acid solution. For every 10 mg of heparosan 2.5 mg of chitosan was added to the supernatant using the 10 mg/ml chitosan solution.
5. The mixture was then stirred for 10 min at room temperature to ensure proper mixing of the resulting solution. This was followed by incubation of the mixture at 4° C. overnight.
6. Chitosan-heparosan polyelectrolyte complex forms a precipitate that settled down and was recovered using centrifugation at 8000 rpm for 1 h.
7. This was followed by washing the precipitate with pH 4.0 DI water and centrifuging it again at 8000 rpm for 1 h.
8. Chitosan loses its cationic nature under basic condition leading to disruption of electrostatic complex, leading to free heparosan in solution and insoluble chitosan. The washed pellet was put in 1M NaOH solution and incubated overnight to recover heparosan in solution. The insoluble chitosan was removed either through filtration or centrifugation at 10000 rpm for 2 h. This step can be coupled with a cation exchange step or an anion exchange step to remove other process impurities leading to further purification of recovered heparosan.

Example 3A

Using the above procedure, heparosan was purified from fermentation broth using DEAE sepharose fast flow resin in column mode followed by precipitation with four volumes of ethanol. The recovered heparosan was then dialyzed using 3500 MWCO membranes against DI water. The dialyzed solution was then freeze-dried following volume reduction using a rotary evaporator.

A 1 mg/ml solution of this purified heparosan was then prepared by dissolving it in pH 4.0 deionized water. Six different samples are prepared by using 10 ml of 1 mg/ml solution and adding varying amounts of chitosan in the range of 2-6 mg using 10 mg/ml chitosan solution in 1% acetic acid. The samples were incubated at 4° C. overnight. The precipitated polyelectrolyte complex was recovered by centrifuging these samples at 8000 rpm for 1 h. A 1M NaOH solution was then added to the pellets obtained without washing with pH 4.0 DI water. Insoluble chitosan was removed by centrifuging at 10000 rpm for 2 h. The recovered samples and the supernatant were then analyzed for presence of heparosan using the carbazole assay.

According to the carbazole assay, 100% recovery of heparosan was achieved at pH 4.0 by addition of 4 mg of chitosan to 10 ml of 1 mg/ml Heparosan solution.

Example 3B

In an additional experiment, supernatant obtained after post-fermentation centrifugation was conditioned by addition of hydrochloric acid to pH 4.0. This was followed by centrifugation at 8000 rpm for 1 h for removal of impurities that precipitate out. The supernatant was then adjusted back to pH 4.0 using 1 M NaOH solution. NMR quantification of this pH-adjusted sample revealed that there was no loss of heparosan in these samples.

These samples were then diluted five times using pH 4.0 DI water. Following this, six samples of 10 ml each were prepared by addition of chitosan in the range of 2-8 mg per sample using 10 mg/ml chitosan solution in 1% acetic acid. The samples were incubated at 4° C. overnight. The precipitated polyelectrolyte complex was recovered by centrifuging these samples at 8000 rpm for 1 h. A 1M NaOH solution was then added to the pellets obtained without washing it with pH 4.0 DI water. Insoluble chitosan was removed by centrifuging at 10000 rpm for 2 h. The recovered samples and the supernatant were then analyzed for presence of heparosan using the carbazole assay. Carbazole assays of the samples showed ~70% purification of heparosan from the fermentation broth.

The invention provides for an efficient purification method for recovering heparosan from fermentation broth. Chitosan employed in this process is cheap, readily available, biocompatible, and biodegradable. These properties make it ideal for use as a precipitant for purification of heparosan, which can be enzymatically modified to intravenously deliverable heparin. The invention also provides for a critical concentrating step, thereby reducing the working volume involved in this process as compared to commonly employed ethanol precipitation steps. The working volumes for ethanol precipitation, for example, in some cases exceeds the fermentation volumes. The biocompatible and biodegradable nature of chitosan makes it much more favorable compared to other polycations which are toxic in nature like, cetylpyridinium chloride (CPC) and Poly(diallyldimethyl ammonium chloride). In addition, this method has the potential for purification of other such polysaccharides such as hyaluronic acid and acidic proteins, as well as DNA.

This invention also provides for a cost effective recovery of bacterial capsular polysaccharide, K5 heparosan, from the fermentation broth using precipitation for potential use in the development of bioengineered heparin. The method employs naturally derived polycations, which are biocompatible and biodegradable, thereby providing an efficient and safe purification technology for intravenously delivered drugs such as heparin. The high yields obtained through this method make it ideal as a concentration step thereby reducing the working volume. The ease of recovery of this step and its compatibility with further steps in the chemoenzymatic synthesis of bioengineered heparin makes it ideal for use as a purification process. This method has potential for removal of other anionic polysaccharides and proteins derived from bacterial fermentation as well as highly charged negative species such as DNA.

What is claimed is:

1. A method of producing substantially pure heparosan from *E. coli* K5, comprising
   (a) culturing *E. coli* K5 in defined medium with glucose as the primary carbon source wherein culturing consists of a batch growth phase and fed batch growth stage, wherein
      (i) the medium used in the batch growth stage comprises (per liter) about 20 g glucose, 10-300 mg thiamine, about 13.5 g $KH_2PO_4$; about 4.0 g $(NH_4)_2HPO_4$, about 1.4 g $MgSO_4.7H_2O$, about 1.7 g citric acid, and about 10.0 mL trace metal solution; wherein the trace metal solution consists essentially of (per L of 5 M HCl) 10.0 g $FeSO_4.7H_2O$, 2.0 g $CaCl_2$, 2.2 g $ZnSO_4.7H_2O$, 0.5 g $MnSO_4.4H_2O$, 1.0 g $CuSO_4.5H_2O$, 0.1 g $(NH_4)_6Mo_7O_{24}.4H_2O$, and 0.02 g $Na_2B_4O_7.10H_2O$ and wherein;
      (ii) the feeding medium used in the fed batch growth stage consists of (per L): 250-1000 g glucose, 20 g $MgSO_4$, 0.15-0.5 g thiamine, and optionally 47 g $KH_2PO_4$, and
      (iii) wherein oxygen is provided by sparged air with or without supplemental oxygen
   (b) binding heparosan to a solid phase with subsequent elution; and
   (c) precipitating heparosan from the eluate;
   wherein said substantially pure heparosan is at least 90% pure.

2. The method of claim 1, wherein dissolved oxygen is maintained at about 20%.

3. The method of claim 1, wherein the temperature is maintained at about 37° C., and the pH is maintained at about 7.

4. The method of claim 3, wherein said pH is maintained by the addition of 29% ammonia solution.

5. The method of claim 1, wherein the medium used in the fed-batch stage is fed at a rate determined by $$Ms(t) = F(t)s_{F(t)} = \left(\frac{\mu}{Y_{\frac{x}{s}}} + m\right)X(t_0)V(t_0)\exp[\mu(t-t_0)]$$

wherein Ms is mass flow rate of the carbon source (g/h); F is feed flow rate (L/h); $S_F$ is carbon substrate concentration in the feed (g/L); X is cell concentration (g/L dcw); m is specific maintenance coefficient (g/g dcw/h); V is culture volume (L); $t_0$ is time of feeding start; t is process time; $\mu$ is specific growth rate ($h^{-1}$); and $Y_{x/s}$ is cell yield on carbon substrate (g/g).

6. The method of claim 1, wherein more than 12 g heparosan per L of culture supernatant is obtained.

7. The method of claim 6, wherein said fermentation is less than 48 hours, not including starter culture.

8. The method of claim 1, wherein the binding and elution step comprises (i) removal of cells; (ii) mixing of an anionic exchange resin with the culture supernatant and removal of the supernatant (iii) washing the resin with 50 mM sodium chloride in sodium acetate buffer at pH 4 (iv) elution with 1 M sodium chloride in sodium acetate buffer at pH 4.

9. The method of claim 1, wherein said binding and elution step comprises: (i) removal of cells; (ii) mixing of a chitosan solution with the culture supernatant; (iii) precipitation of the chitosan and isolation of the precipitate; (iv) washing the chitosan; (v) elution of heparosan with about 1M NaOH.

10. The method of claim 1, wherein said precipitating heparosan from the eluate comprises ethanol precipitation.

11. The method of claim 1, further comprising depyrogenation with hydrogen peroxide.

12. The method of claim 1, wherein the heparosan is less than 1% DNA and less than 2% protein.

13. The method of claim 1, wherein the heparosan has a number average molecular weight of about 58,000 Da, a weight average molecular weight of about 84,000 Da, and polydispersity index (PDI) of about 1.4.

14. The method of claim 1, wherein the heparosan is at least 95% pure.

15. Heparosan produced by the method of claim 1.

16. Heparin manufactured from the heparosan of claim 15.

* * * * *